United States Patent [19]

Dove et al.

[11] Patent Number: 4,904,261

[45] Date of Patent: Feb. 27, 1990

[54] SPINAL IMPLANTS

[75] Inventors: John Dove, Park Hill, England; Philip H. Hardcastle, Nedlands, Australia; John K. Davis, Endon; Brian M. King, Longton, both of England

[73] Assignee: A. W. Showell (SURGICRAFT) Limited, Redditch, England

[21] Appl. No.: 228,331

[22] Filed: Aug. 4, 1988

[30] Foreign Application Priority Data

Aug. 6, 1987 [GB] United Kingdom ............... 8718627

[51] Int. Cl.$^4$ ............................................. A61F 2/52
[52] U.S. Cl. ............................................. 623/17
[58] Field of Search .................................... 623/16, 17

[56] References Cited

U.S. PATENT DOCUMENTS 4,714,469 12/1987 Kenna ................................. 623/17
4,759,769 7/1988 Hedman ............................. 623/17

Primary Examiner—Richard J. Apley
Assistant Examiner—James Prizant
Attorney, Agent, or Firm—R. A. Giangiorgi

[57] ABSTRACT

A spinal implant, e.g., to replace an excised disc, comprises a rigid generally horseshoe shape of biocompatible material, such as carbon-fibre reinforced plastics, having upper and lower planar faces (10, 11) converging towards the ends (12) of the horseshoe, and at least one hole (13, 14) from each planar face (10, 11) emerging in the outer curved face (15) of the horseshoe, to enable the horseshoe to be fixed by screws inserted through one or more selected holes in each plurality (13, 14) from the ends in the outer curved face (15) into respective adjacent vertebrae, with the screw heads bearing against shoulders (18), and with the space bounded by the inner curved face (17) of the horseshoe available for the insertion of bone graft or a bone graft substitute.

7 Claims, 2 Drawing Sheets

SPINAL IMPLANTS

This invention relates to spinal implants for use as anterior fixation devices to supplement anterior spinal fusions. In general a single level anterior spinal fusion suffices, but—if clinically indicated—more than one implant (and fusion) could be used at different levels.

A single level anterior spinal fusion is a well established surgical technique for the treatment of certain spinal problems. Excision of a disc and fusion with bone graft, without internal fixation against rocking and rotation, not infrequently leads to dislodgement of the graft or sinking in of the graft and non-union with the vertebrae. Until now there has been no satisfactory implant to cope with this particuar problem.

The object of the invention is to provide an implant that can be contained substantially within the confines of the anterior vertebral column and act as a spacer between adjacent vertebrae at the peripheries of the ends thereof which are structurally the strongest parts.

According to one aspect of the the present invention, a spinal implant comprises a rigid generally horseshoe shape of biocompatible material having upper and lower planar faces converging towards the ends of the horseshoe, and at least one hole from each planar face emerging in the outer curved face of the horseshoe.

After insertion of the implant between adjacent vertebrae, with the gap between the ends directed towards the spinal canal, the implant is secured as by pegs or bollards or by fixation pins or screws inserted through the holes from the ends in the outer curved face of the horseshoe and into the respective vertebrae, and the gap between the ends of the horseshoe forms an opening for the insertion of bone graft into the central space bounded by the inner curved face of the horseshoe forming a cavity also bounded by the adjacent vertebrae.

Thus, the implant supports the vertebrae inwards from their peripheries, leaving the central portions of the end faces of the vertebrae available for the seating of bone graft, and relieves the bone graft of loads (otherwise created by relative rocking and/or rotation of the vertebrae) that could result in dislodgement of the graft or sinking in of the graft and non-union with the vertebrae.

The implant may be formed of carbon-fiber reinforced plastics, such as epoxy resin, or other biocompatible material, such as an inert or bio-degradable fiber-reinforced composite, or calcium nitride. Examples of other suitable materials are metals such as titanium, possibly with hydroxyapatite, and stainless steel, or ceramics, polyethylene hydroxyapatite and polyethylene hydroxybutyrate.

Pluralities of holes are preferably provided from each planar face to the outer curved face of the horseshoe, conveniently in alternation between one planar face and the other, say four in one and three in the other, for selective use of any one (or more) in each planar face for insertion of fixation pins or screws.

An embodiment of the invention will now be described, by way of example only, with reference to the accompanying drawings, in which.

Figure 1:
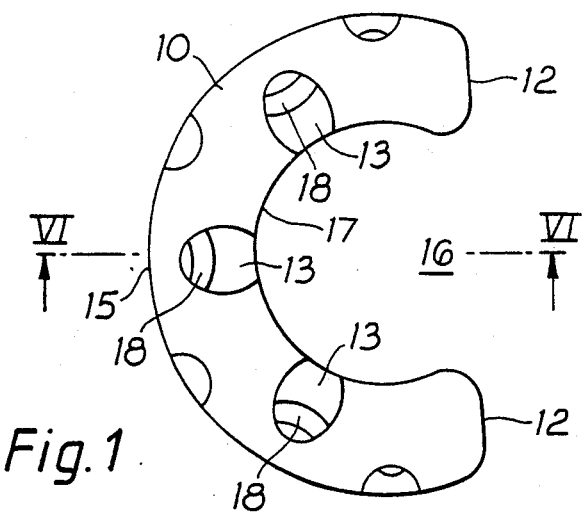
FIG. 1 is a plan view of the "horseshoe", i.e., its upper planar face.
Figure 2:
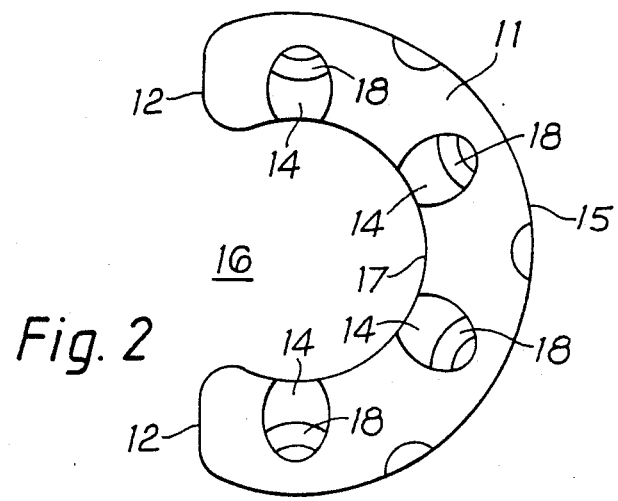
FIG. 2 is an underneath view, i.e., of its lower planar face.
Figure 3:
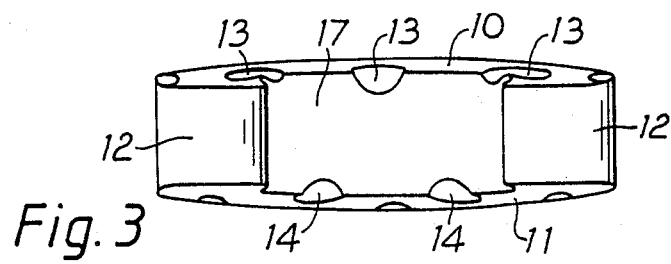
FIG. 3 is a view from the ends of the "horseshoe"
Figure 4:
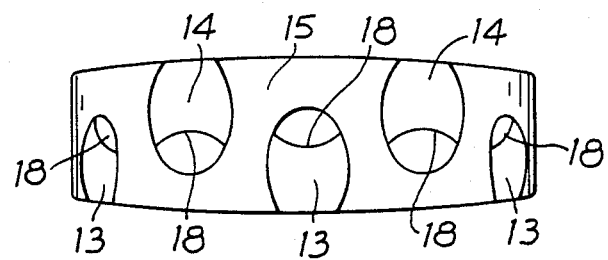
FIG. 4 is the opposite view to FIG. 3.
Figure 5:
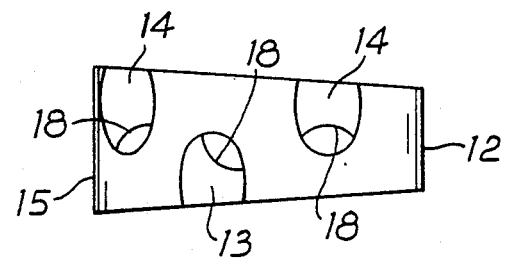
FIG. 5 is a side view (the other side corresponds)
Figure 6:
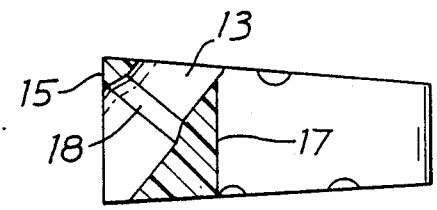
FIG. 6 is a section from the line VI—VI of FIG. 1.

The "horseshoe" spinal implant shown in the drawings is intended to be contained substantially within the confines of the anterior vertebral column and act as a spacer between adjacent vertebrae at the peripheries of the ends thereof which are structurally the strongest parts. It consists of biocompatible material, such as carbon-fiber-reinforced plastics, and has upper and lower planar faces 10, 11 respectively converging towards the ends 12 of the horseshoe, and pluralities of holes 13, 14 respectively are provided from each planar face (10, 11 respectively) emerging in the outer curved face 15 of the horseshoe, to enable the horseshoe to be fixed between adjacent vertebrae (not shown) as by fixation screws (not shown) inserted through one or more selected holes in each plurality, from the ends of the holes in the outer curved face 15 and into the respective vertebrae, and the gap 16 between the ends 12 of the horseshoe forms an opening for the insertion of bone graft into the central space bounded by the inner curved face 17 of the horseshoe forming a cavity also bounded by the adjacent vertebrae. Each hole 13, 14 has a shoulder 18 (between portions of slightly different diameter) against which the head of a screw can bear.

A variety of sizes with regard to internal and external diameter and/or thickness and/or taper are preferably provided for selection to suit individual spinal cases, including implants at different levels. In addition to being used as a disc replacement, a larger size of implant in accordance with the invention may conceivably be used as a vertebrae body replacement.

The central space may alternatively be fitted with an insert formed of a bone graft substitute.

According to another aspect of the present invention, a spinal implant has similar features to the embodiment described above except that there are no holes in either face but instead each face has ridges generally parallel to the plane containing the ends of the horseshoe, which ridges afford a grip on adjacent vertebrae when implanted in a spine.

We claim:

1. A spinal implant comprising a rigid generally horseshoe shape of biocompatible material having upper and lower planar faces converging towards the ends of the horseshoe, and at least one hole from each planar face emerging in the outer curved face of the horseshoe.

2. A spinal implant as in claim 1, wherein pluralities of holes are provided from each planar face to the outer curved face of the horseshoe.

3. A spinal implant as in claim 2, wherein the holes are in alternation between one planar face and the other.

4. A spinal implant as in claim 3, wherein there are four holes in one planar face and three in the other.

5. A spinal implant as in claim 1, wherein each hole has a shoulder against which the head of a screw can bear.

6. A spinal implant as in claim 1, wherein the central space bounded by the inner curved face of the horseshoe is fitted with an insert formed of a bone graft substitute.

7. A spinal implant comprising a rigid generally horseshoe shape of biocompatible material having upper and lower planar faces converging towards the ends of the horseshoe and each face having ridges generally parallel to the plane containing the ends of the horseshoe.

* * * * *